United States Patent [19]

Oude Alink

[11] 3,931,191

[45] Jan. 6, 1976

[54] CONVERSION OF TETRAHYDROPYRIMIDINES TO PYRIDINES

[75] Inventor: Bernardus A. Oude Alink, St. Louis, Mo.

[73] Assignee: Petrolite Corporation, St. Louis, Mo.

[22] Filed: Aug. 1, 1973

[21] Appl. No.: 384,440

Related U.S. Application Data

[63] Continuation-in-part of Ser. No. 292,494, Sept. 27, 1972.

[52] U.S. Cl. ..... 260/290 P; 260/283 SY; 260/297 R
[51] Int. Cl.² .................................. C07D 213/04
[58] Field of Search ........................... 260/290, 297

[56] References Cited

OTHER PUBLICATIONS

Asinger et al., Angew. Chem., Vol. 70, p. 680–681, (1958).

*Primary Examiner*—Harry I. Moatz
*Attorney, Agent, or Firm*—Sidney B. Ring; Hyman F. Glass

[57] ABSTRACT

A process of converting 2,3,4,5-tetrahydropyrimidines containing at least 1 hydrogen in the 2-position and at least one methylene group in the 4-position to corresponding pyridines which comprises heating said tetrahydropyrimidines to a temperature sufficiently high to remove ammonia and hydrogen so as to form said pyridines.

5 Claims, No Drawings

CONVERSION OF TETRAHYDROPYRIMIDINES TO PYRIDINES

This application is a continuation-in-part of Ser. No. 292,494 filed on Sept. 27, 1972.

In Ser. No. 292,494 filed on Sept. 27, 1972 there is described and claimed substituted 2, 3, 4, 5-tetrahydropyrimidines (THP)

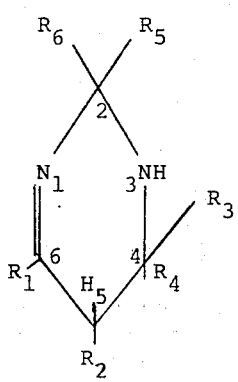

which are prepared by the following reactions:
1. The reaction of a carbonyl compound (ketone or aldehyde) with ($NH_3$ or $NH_4OH$) and a sulfur-containing catalyst.
2. The reaction of an $\alpha$, $\beta$-unsaturated ketone and a carbonyl compound and $NH_3$ (or $NH_4OH$) without a catalyst.
3. Reaction of an 60 , $\beta$-unsaturated ketone, a 1-amino-alcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

such as cyclohexanone, cyclopentanone, substituted derivatives thereof such as alkyl-cyclohexanone, dialkyl-cyclohexanone.

I have discovered that the tetrahydropyrimidines of said Ser. No. 292,494 can be converted to substituted pyridines according to the following equation.

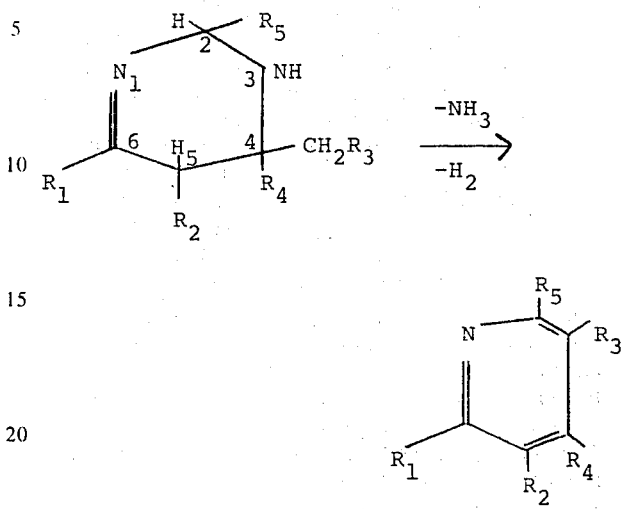

provided the 2-position of THP contains at least 1 hydrogen and one of the groups attached to carbon 4 of THP has at least one methylene group.

The meaning of $R_1$, $R_2$, $R_3$, $R_4$, $R_5$ are the same as stated above.

The reaction is carried by heating THP at a temperature sufficiently high to remove ammonia and hydrogen so as to cause rearrangement to the pyridine compound. In general, the temperature employed is from about 60° – 400°C. or higher, such as from about 75° – 350°, but preferably from about 90° – 250°C. with an optimum of about 200° to 250°C. Reduced pressure may be employed as desired so as to aid in removal of $NH_3$ and $H_2$.

The reaction can be carried out with or without a catalyst. Where a catalyst is employed it is generally of the Lewis acid type. Typical catalysts include salts, such as of inorganic or organic acids for example ammonium or amine salts of the formula $$\text{Ⓝ} \cdot X$$

where Ⓝ is ammonium or amine and X is an anion for example a halide (Cl, Br, F, I), a carboxylic acid, a sulfonic acid, etc. Illustrative examples include $NH_4$ acetate   $NH_4$ I
$NH_4$ Cl   $NH_4$ benzenesulfonate, etc.
$NH_4$ Br
Zinc halides such as zinc chloride, silica, etc.
Other catalysts include $AlCl_3$, $FeCl_3$, $PbO$, $Al_2O_3$, etc.

The following examples are presented by way of illustration and not of limitation.

EXAMPLE 1

2-Propyl - 3,5-diethyl pyridine

In a pressure reactor was placed a 453.6g of butyraldehyde and 17g of ammonium chloride. To the mixture was added, with cooling, 85g of ammonia gas, at such a rate that a reaction temperature of 40°–45°C. was maintained. After the addition was completed (0.5 hrs), cooling was discontinued and the reaction mixture was stirred for 2 hrs. at ambient temperature. The aqueous phase produced was removed and the organic layer was dried to yield 398.2g (97% of theory) of 2,4-di-n-propyl-5-ethyl-2,3,4,5-tetrahydropyrimidine.

The product was then heated to 235°C. over a ½ hr. period and kept at 235°C. for 2½ hrs. The resulting product 346.2g of material (96.3% of theory) was distilled to yield 298g of 2-propyl-3,5-diethylpyridine (80% of theory based on butyraldehyde) $b._{760}235°-242°C.$; nuclear magnetic resonance spectrum, solvent $CCl_4$, δ in ppm, 8.38 d., 1H; 7.38 d. 1H; 2.70 and 2.67 m's, 6H; 1.80 m, 2H; 1.18 t. 6H; and 0.97t, 3H.

Anal. calc.ed for $C_{12}H_{19}N$; N, 7.91; Found; N, 7.8.

EXAMPLE 2

2-Propyl-3,5-diethyl pyridine

In a pressure reactor was placed 361.1g of butyraldehyde. Over a 1 hr period 54g of ammonia gas was added, while a temperature of 30-35°C. was maintained by cooling of the reaction mixture. After the addition was completed stirring was continued for 1 hr. The water produced was removed under diminished pressure to yield 327g. of 2,4-di-n-propyl-5-ethyl-2,3,4,5-tetrahydropyrimidine.

The product was heated over a 1 hr period to reflux. Ammonia and hydrogen gas were evolved. Distillation yielded after a forerun of 61.3g of mainly butyraldehyde, 222g of 2-propyl-3,5-diethylpyridine, identical to the pyridine described in example 1.

EXAMPLE 3

2-Ethyl-3,5-dimethylpyridine

In a pressure reactor was placed 18g of ammonium chloride and 341.1g. of propionaldehyde. To the mixture was added over a 1 hr. period 80g. of ammonia gas at such a rate that a temperature of 28°-35°C. was maintained. After the addition was completed, the mixture was stirred for an additional 3 hrs. at ambient temperature. The product was taken up in chloroform. The aqueous layer removed and the chloroform solution evaporated under diminished pressure to yield 300.6g. of 2,4-diethyl-5-methyl-2,3,4,5-tetrahydropyrimidine.

A sample of 204.6g. of 2,4-diethyl-5-methyl-2,3,4,5-tetrahydropyrimidine and 0.8g. of ammonium chloride were heated over a 3/4 hr. period to reflux and refluxed for 5 hrs. Distillation yielded 125.1g of 2-ethyl-3,5-dimethylpyridine. $b_{760}195°-205°C.$; nuclear magnetic resonance spectrum, no solvent, δ in ppm, 8.17, m, 1H; 7.03 m, 1H; 2.08 s, 6H; 2.68 q, 2H; 1.23 t, 3H.

Anal. Calc.ed for $C_9H_{13}N$; N, 10.4; Found; N, 10.3.

EXAMPLE 4

2,4-Dimethyl-6-n-propylpyridine

A sample of 196g. of mesityloxide and 144g. of butyraldehyde were placed in a 1 pt. pressure reactor. To the mixture was added over a 2 hr. period, 79g. of ammonia gas. After the addition was completed, the mixture was stirred for 18 hrs. at ambient temperature. The aqueous layer produced was removed and the product distilled under diminished pressure to yield 303.8g. of 2-n-propyl-4,4,6-trimethyl-2,3,4,5-tetrahydropyrimidine, $b_{20}88°-89°C.$ A sample of 100.4g. of 2-n-propyl-4,4,6-trimethyl-2,3,4,5-tetrahydropyrimidine and 0.5g. of ammonium acetate was heated to reflux over a 1 hr period and refluxed for 1 hr. Distillation of the product yielded 36.7g. of 2.4-dimethyl-6-n-propylpyridine, $b_{760}205°-214°C.$; nuclear magnetic resonance spectrum, solvent $CCl_4$. δ in ppm.; 6.67, s, 2H; 2.55, q, 2H; 2.37, s, 3H; 2.17, s, 3H; 1.58, m, 2H; 0.91 t. 3H.

Anal. Calc.ed for $C_{10}H_{15}N$; N, 9.38; Found; N, 9.3.

In order to avoid repetitive detail and since all examples were prepared in the manner described in example 1, the following substituted pyridines which were prepared from the corresponding substituted 2,3,4,5-tetrahydropyrimidines are presented in tabular form in the following table.

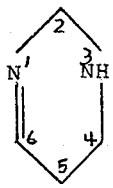 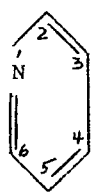

| Ex. No. | Starting Material Group Substituted in Tetrahydropyrimidine | Products Groups substituted in pyridine |
|---|---|---|
| 5 | 4,4,6-trimethyl | 2,4-dimethyl |
| 6 | 2-methyl-4,4,6-trimethyl | 2,4,6-trimethyl |
| 7 | 2-isopropyl-4,4,6-trimethyl | 2-isopropyl-4,6-dimethyl |
| 8 | 2-n-hexyl-4,4,6-trimethyl | 2-n-hexyl-4,6-dimethyl |
| 9 | 2-n-octyl-4,4,6-trimethyl | 2-n-octyl-4,6-dimethyl |
| 10 | 2-isopropyl-4-n-propyl-5-ethyl | 2-isopropyl-3,5-diethyl |
| 11 | 2-isopentyl-4,4,6-trimethyl | 2-isopentyl-4,6-dimethyl |
| 12 | 2,4-di-n-hexyl-5-pentyl | 2-n-hexyl-3,5-di-n-pentyl |
| 13 | 2-phenyl-4,4,6-trimethyl | 2-phenyl-4,6-dimethyl |
| 14 | 2-p-methoxyphenyl-4,4,6-trimethyl | 2-p-methoxyphenyl-4,6-dimethyl |
| 15 | 2-furyl-4,4,6-trimethyl | 2-furyl-4,6-dimethyl |
| 16 | 2-benzyl-4,4,6-trimethyl | 2-benzyl-4,6-dimethyl |

The compositions of this invention are useful as corrosion inhibitors, biocides, fuel additives, fuel antifoulants, scale inhibitors, antistatic agents, chelating agents, etc.

It will be apparent that various changes and modifications may be made in the invention described herein without departing from the scope of the invention. It is intended, therefore, that all matter shall be interpreted as illustrative and not as limitative.

I claim:

1. The process of converting a 2,3,4,5-tetrahydropyrimidine of the formula

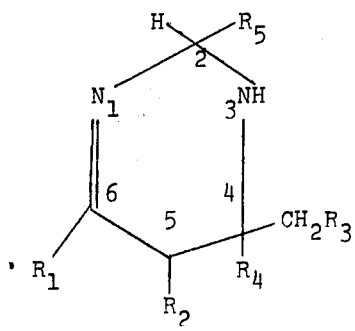

wherein $R_1$, $R_2$, $R_3$, $R_4$, and $R_5$ may be the same or different are hydrogen, alkyl, aryl, cycloalkyl, alkaryl, aralkyl or heterocyclic to the corresponding pyridine which comprises heating said tetrahydropyrimidine to a temperature between 75°C. and 350°C. sufficently high to remove ammonia and hydrogen so as to form said pyridine.

2. The process of claim 1 where a Lewis Acid catalyst is employed.

3. The process of claim 2 where the Lewis Acid catalyst is an ammonium salt.

4. The process of claim 3 where the ammonium salt is an ammonium salt of an inorganic or an organic acid.

5. The process of claim 4 where the ammonium salt is ammonium chloride or ammonium acetate.

* * * * *